US008314935B2

(12) United States Patent
Handa et al.

(10) Patent No.: US 8,314,935 B2
(45) Date of Patent: Nov. 20, 2012

(54) TARGET SUBSTANCE-DETECTING APPARATUS AND TARGET SUBSTANCE-DETECTING METHOD

(75) Inventors: Yoichiro Handa, Tokyo (JP); Tomohiro Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 333 days.

(21) Appl. No.: 12/672,067

(22) PCT Filed: Sep. 25, 2008

(86) PCT No.: PCT/JP2008/067871
§ 371 (c)(1),
(2), (4) Date: Feb. 3, 2010

(87) PCT Pub. No.: WO2009/041709
PCT Pub. Date: Apr. 2, 2009

(65) Prior Publication Data
US 2011/0164252 A1    Jul. 7, 2011

(30) Foreign Application Priority Data
Sep. 28, 2007    (JP) .................................. 2007-254744

(51) Int. Cl.
*G01J 3/447* (2006.01)
*G01N 21/55* (2006.01)
(52) U.S. Cl. ......... 356/445; 356/322; 356/327; 356/448
(58) Field of Classification Search .......... 356/445–448, 356/450–458
See application file for complete search history.

(56) References Cited

U.S. PATENT DOCUMENTS

| | | | | |
|---|---|---|---|---|
| 4,997,278 A * | 3/1991 | Finlan et al. | .................. | 356/128 |
| 5,991,488 A * | 11/1999 | Salamon et al. | .............. | 385/129 |
| 7,136,166 B2 * | 11/2006 | Yamada et al. | ............... | 356/445 |
| 7,684,044 B2 * | 3/2010 | Sekiguchi et al. | ............ | 356/445 |
| 7,826,042 B2 * | 11/2010 | Yamamichi et al. | ............ | 356/72 |
| 2009/0109422 A1 | 4/2009 | Handa et al. | | |
| 2009/0117669 A1 | 5/2009 | Yamamichi et al. | | |
| 2009/0128822 A1 | 5/2009 | Yamamichi et al. | | |

OTHER PUBLICATIONS

Nishikawa et al. Development of New Localized Surface Plasmon Resonance Sensor with Nanoimprinting Technique:, Proceedings od the 1$^{st}$ IEEE International Conference on Nano/Micro Engineered and Molecular Systems, Jan. 2006, pp. 262-265.*

(Continued)

*Primary Examiner* — Gregory J Toatley
*Assistant Examiner* — Jarreas C Underwood
(74) *Attorney, Agent, or Firm* — Fitzpatrick, Cella, Harper & Scinto (57) ABSTRACT

A target substance-detecting apparatus for detecting a target substance in an analyte comprises a detecting device having a substrate and metal structures capable of causing a plasmon resonance arranged thereon, an illumination optical system for illuminating an incident light containing a polarization component polarized in a first direction onto the detecting device to cross the arranged metal structures, a light-receiving device for receiving light containing the polarization component polarized in the first direction and transmitted through or reflected by the detecting device, and an arithmetic unit for calculating on signals from the light-receiving device to analyze a characteristic of the analyte; the metal structures arranged at first intervals not more than $\frac{1}{10}$ of a plasmon resonance wavelength in lines in the first direction and at second intervals not less than $\frac{1}{4}$ of the plasmon resonance wavelength and not more than the wavelength in lines parallel in a second direction.

4 Claims, 10 Drawing Sheets

OTHER PUBLICATIONS

Quidant et al, "Optical Sensing Based on Localized Surface Plasmons", Proc of SPIE, vol. 5840, 2005, pp. 272-283.*

PCT International Search Report, International Application No. PCT/JP2008/067871, Mailing Date Jun. 3, 2009.

Haes, et al., "A Nanoscale Optical Biosensor: The Long Range Distance Dependence of the Localized Surface Plasmon Resonance of Noble Metal Nanoparticles", J. Phys. Chem. B, vol. 108, 2004, pp. 109-116.

Bouhelier, et al., "Electromagnetic Interactions in Plasmonic Nanoparticle Arrays", J. Phys. Chem. B, vol. 109, 2005, pp. 3195-3198.

Rechberger, et al., "Optical properties of two interacting gold nanoparticles", Optics Communications, vol. 220, 2003, pp. 137-141.

Nishikawa, et al., Development of New Localized Surface Plasmon Resonance Sensor with Nanoimprinting Technique:, Proceedings of the 1st IEEE International Conference on Nano/Micro Engineered and Molecular Systems, Jan. 2006, pp. 262-265.

Quidant, et al., "Optical sensing based on localized surface plasmons", Proc. of SPIE, vol. 5840, 2005, pp. 272-283.

* cited by examiner

FIG. 12

TARGET SUBSTANCE-DETECTING APPARATUS AND TARGET SUBSTANCE-DETECTING METHOD

TECHNICAL FIELD

The present invention relates to a target substance-detecting apparatus for detecting a target substance in an analyte, and a method for detecting the target substance.

BACKGROUND ART

With increasing interests in problems of health, environment, and food safety, improvements are required of methods for detecting the substances relating to the above problems (chemical substances including substances related to living body (hereinafter referred to as a "target substances")). For detection of such a target substance, a higher sensitivity of detection is often required. This is because the available amount of the analytes containing the target substance is often very small, and further the target substance is contained in an extremely small amount in the analyte with coexistence of various substances, especially in detection of a protein in a blood. Thus, in the detection of the target substance, high-sensitive detection technique is demanded for detection of an extremely small amount of the target substance in a small amount of an analyte.

To meet the above requirement, methods of measurement are being developed which utilize plasmon resonance with metal particles or a metal structure. On illumination of an incident light in a particular wavelength range onto metal particles or a metal structure, resonance occurs in a limited wavelength range to cause increase of the scattering or absorbance of the incident light. This phenomenon is localized plasmon resonance (hereinafter referred to simply as "plasmon resonance"). The wavelength in which the absorbance becomes maximum is called a plasmon resonance wavelength. At the plasmon resonance wavelength, the transmittance of the incident light through the metal particles or metal structure is decreased significantly. This plasmon resonance wavelength depends on the refractive index of the medium surrounding the metal particles or metal structure. Therefore, the plasmon resonance wavelength can be changed by gathering a target substance from the analyte in the neighbourhood of the metal structure. In other words, the absorption spectrum of the incident light illuminated onto the metal structure can be changed by the target substance gathered in the neighbourhood of the metal structure.

In detection of the substance by utilizing the plasmon resonance with a metal particle or metal structure, usually are detected the shift of the absorption spectrum of the illuminated incident light (i.e., the shift of the resonance wavelength) or change of the absorbance at a specified wavelength. Therefore, a larger shift of the plasmon resonance wavelength or a smaller peak width of the absorption spectrum is desirable for detection at higher sensitivity.

A document, J. Phys. Chem. B, 2004, vol. 108, No. 1, pp. 109-116, describes that the shift of the absorption spectrum depends on the increase of the electric field intensity caused by light irradiation in the neighbourhood of the metal structure: a larger increase of the electric field intensity contributes more the shift of the absorption spectrum.

A document, J. Phys. Chem. B, 2005, vol. 109, No. 8, pp. 3195-3198, describes that a shorter distance between the metal structures causes increase of the electric field strength in the neighbourhood of the metal structures. A document, Optics Communications, 2003, vol. 220, No. 1-3, pp. 137-141, describes that the shorter distance between the metal structures increases the peak width of the absorption spectrum.

A document, J. Phys. Chem. B, 2004, vol. 108, No. 1, pp. 109-116, describes that a random distribution of gold nanoparticles for causing the plasmon resonance makes random the distance between the gold nanoparticles to broaden the resonance conditions depending on the distance between the gold particles to lower the detection sensitivity, since the conditions of the plasmon resonance depend on the distance between the gold particles.

According to the above documents, J. Phys. Chem. B, 2005, vol. 109, No. 8, pp. 3195-3198 and Optics Communications, 2003, vol. 220, No. 1-3, pp. 137-141, the smaller intervals between the metal structures can increase the electric field strength between the metal structures and enables increase of the shift of the plasmon resonance wavelength, but can increase the peak width of the absorption spectrum. Thus, the increase of the shift of the plasmon resonance wavelength and decrease of the peak width of the absorption spectrum cannot be achieved simultaneously. Therefore, it is not easy to provide a detection apparatus for detecting a target substance with a high sensitivity.

To solve the above problems, the present invention intends to provide an apparatus for detecting a target substance at a high sensitivity, and a method for detection employing the detecting apparatus.

DISCLOSURE OF THE INVENTION

The present invention is directed to a target substance-detecting apparatus for detecting a target substance in an analyte, comprising: a detecting device having a substrate on which metal structures capable of causing a plasmon resonance are arranged, an illumination optical system having a mechanism for illuminating an incident light containing a polarization component polarized in a first direction onto the detecting device to cross the arranged metal structures in the detecting device, a light-receiving device for receiving light containing the polarization component polarized in the first direction and transmitted through or reflected by the detecting device, and an arithmetic unit for calculating on signals from the light-receiving device to analyze a characteristic of the analyte;

the metal structures being arranged at first intervals in lines in the first direction and at second intervals in lines parallel in a second direction intersecting the first direction, the first intervals being not more than $\frac{1}{10}$ of a plasmon resonance wavelength, and the second interval being not less than $\frac{1}{4}$ of the plasmon resonance wavelength and not more than the plasmon resonance wavelength.

The metal structures can be arranged in the first direction and in the second direction, the first direction and the second direction being perpendicular to each other.

The illumination optical system can comprise a unit for illuminating an incident light polarized in the first direction.

The structure particle of the metal structures can have a size of not smaller than 20 nm and not larger than 100 nm.

The present invention is directed to a method for detection of a target substance for detecting a target substance in an analyte, comprising the steps of:

bringing the analyte into contact with a detecting device having a substrate on which a metal structures capable of causing a plasmon resonance are arranged, illuminating an incident light containing a polarization component polarized in a first direction onto the detecting device to cross the arranged metal structures in the detecting device, receiving light containing the polarization component polarized in the first direction and transmitted through or reflected by the detecting device, and calculating on signals from the light-receiving device to analyze a characteristic of the analyte.

The present invention improves the sensitivity of detection of a target substance in an analyte.

Further features and aspects of the present invention will become apparent from the following description of exemplary embodiments with reference to the attached drawings.

The reference numerals denotes constitutional members as follows: 101, a detecting device; 102, an illumination optical system; 103, a light-receiving device; 104, an arithmetic unit; 202, a substrate; 203, a metal structure; 204, a target-substance-capturing body (substance-trapping member); 302, a plasmon resonance wavelength; 402, a first interval; 403, a second interval; 404, an incident light; 405, a polarization direction; 406, a first direction; 407, a second direction; 1001, a detecting device; 1002, a quartz substrate; 1003, a gold structure; 1004, an illumination optical system; 1005, a halogen lamp; 1008, an incident light; 1009, a transmitted light; 1010, a spectrometer; 1011, an arithmetic unit; 1101, a polarization direction; 1203, a spectroscopic optical system; 1207, a display unit; 1208, a central processing unit (CPU).

BEST MODE FOR CARRYING OUT THE INVENTION

Embodiments of the present invention are described below with reference to drawings.

Figure 1:
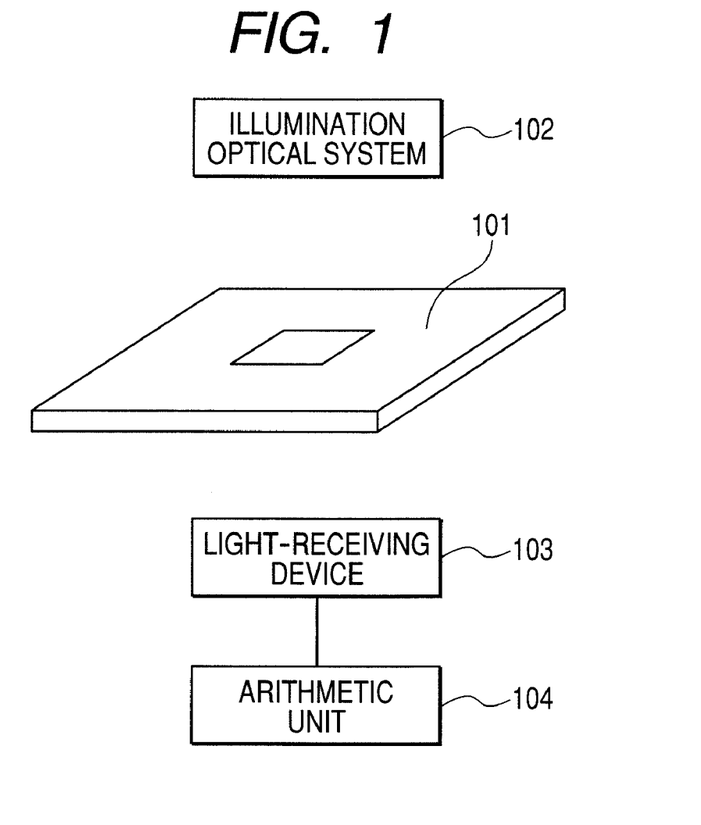
FIG. 1 illustrates schematically a constitution of a target-substance-detecting apparatus of the present invention.

FIG. 1 illustrates schematically a constitution of a target-substance-detecting apparatus of the present invention. This target substance-detecting apparatus comprises detecting device 101, illumination optical system 102 for illuminating an incident light to detecting device 101, light-receiving device 103 for receiving the light through detecting device 101, and an arithmetic unit 104 for processing signals derived by light-receiving device 103.

In this embodiment, the transmitted light through the detecting device is received by the light-receiving device. Otherwise, a reflected light may be received to detect the target substance. In this case, the light-receiving device is placed to receive the light reflected by the detecting device.

Detecting device 101, illumination optical system 102, light-receiving device 103, and arithmetic unit 104 are described below in detail.

(Detecting Device)

Figure 2:
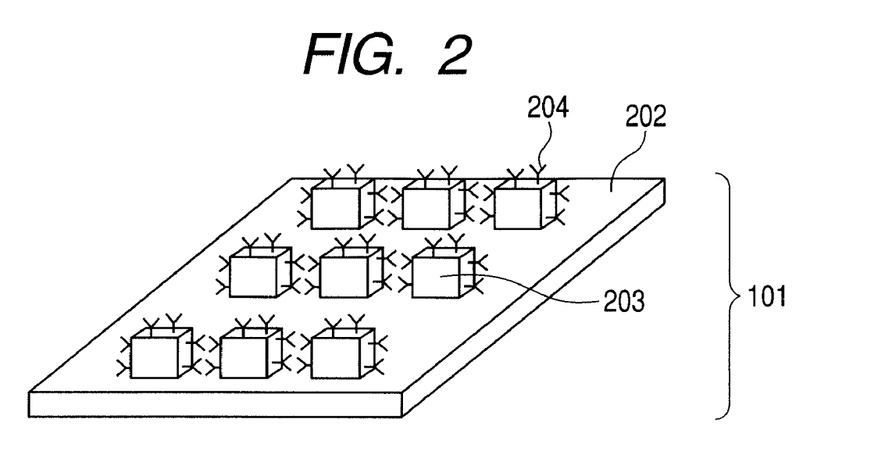
FIG. 2 is a perspective view illustrating a constitution of detecting device 101 in FIG. 1.

FIG. 2 is a perspective view illustrating a constitution of detecting device 101. Detecting device 101 is constituted of substrate 202, a plurality of metal structures 203 placed on the surface of substrate 202. Metal structures 203 respectively immobilize target-substance-capturing-bodies 204 for capturing specifically the target substance. Although, in FIG. 2, no target-substance-capturing-bodies 204 are immobilized on the front face of metal structures 203, target-substance-capturing-bodies 204 may be immobilized in the front face. Metal structures 203 may be bonded onto substrate 202 with interposition of an adhesive layer.

Substrate 202 may be made of any material and in any shape, insofar as the substrate has a face for placing metal structures 203. The substrate has preferably a high transmittance to light in the wavelength range utilized for the detection (the light being referred to as "detecting light"). More preferably, substrate 202 has a refractive index approximate to that of the medium existing in the neighbourhood of metal structures 203 in the detection of the target substance. Thereby the plasmon resonance conditions at the interface between the metal structure and the surrounding medium, and the plasmon resonance conditions at the interface between substrate 202 and metal structures 203 can be brought close to each other to prevent broadening of the plasmon resonance conditions and to decrease the peak width of the absorption spectrum of the incident light introduced to detecting device 101. The refractive index of substrate 202 may be different from that of the surrounding medium, insofar as the peak width of the absorption spectrum can be narrowed sufficiently.

Materials highly transparent to the detecting light include silica, quartz, polymethyl methacrylate (PMMA), polystyrene, amorphous fluororesin, and indium-tin oxide (ITO).

Metal structures 203 are formed from a metal capable of causing a plasmon resonance. The metal includes specifically gold, silver, copper, aluminum, platinum, zinc, alloys constituted of two or more of these elements, and alloys containing at least one of the above elements. Gold and silver are preferred which cause remarkable plasmon resonance.

Figure 3:
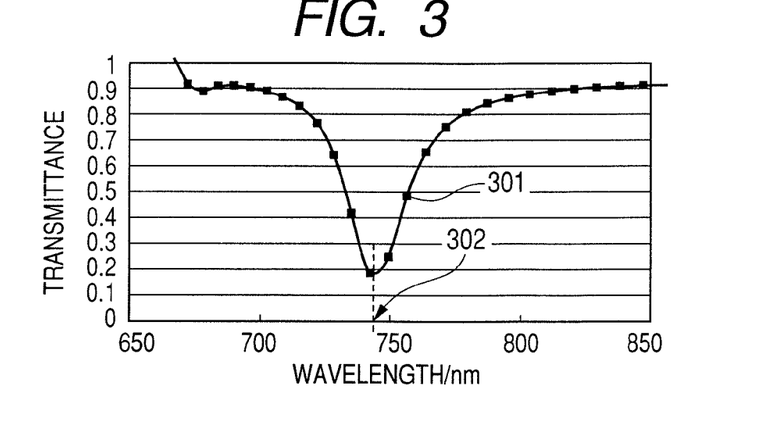
FIG. 3 is a graph showing a transmission spectrum of the transmitted light through the detecting device in FIG. 1.

The plasmon resonance wavelength in the present invention is defined as the wavelength where the transmittance becomes the minimum when light of a broad band is illuminated onto metal structures 203. FIG. 3 is a graph showing a transmission spectrum of the light through detecting device 101.

In detecting device 101, rectangular gold particles having sides of 100 nm and heights of 50 nm are arranged at intervals of 400 nm in a square lattice. Water (refractive index: 1.3350) as the medium surrounds the gold.

In this example, as illustrated in FIG. 3, transmission spectrum 301 becomes the minimum at wavelength of 745 nm. That is, in this example, the plasmon resonance wavelength 302 is 745 nm.

The plasmon resonance wavelength depends on the kind of the metal, size, and arrangement of the metal particles of metal structures 203. Therefore, the kind of the metal, size, and arrangement of the metal particles of metal structures 203 is selected to raise the detection sensitivity to the target substance.

The shape of the particle of metal structures 203 is not limited: the shape may be spherical, or nearly spherical, in a non-polygonal shape. Otherwise, the structure particle may be in a shape of a part of a sphere or sphere-like matter; a cylinder; a polygonal prism; a circular cone; a pyramid; a thick ring; a thick sharp shape (#), a thick cross-in-circle mark shape, and the like. Metal structures 203 may be constituted of spherical metal particles, or polyhedral metal particles.

Regarding the size of metal structure particle 203, the larger the change of the volume of the captured target substance relative to that of the metal structure particle 203, the larger could be the change of the refractive index of the medium surrounding the metal structures 203. This increases the change of the plasmon resonance conditions to enable high-sensitive detection of a target substance. In other word, the size of metal structure particle 203 is preferably smaller. However, extremely small size of metal structure particle 203 results in a small change of the absorbance at the specific wavelength by trapping of the target substance, and makes difficult the detection of the degree of the change of the absorption spectrum.

Further, to increase the shift of the absorption spectrum, the trapping of the target substance by the substance trap 204 should cause sufficient change of plasmon resonance wavelength of metal structures 203. That is, the region in which the plasmon resonance wavelength changes sufficiently in response to the change of the surrounding medium and the region in which the target substance is trapped (the region containing target substance trap 204) correspond to each other. The regions are adjusted to correspond nearly to the region where the electric field caused by introduction of an incident light is strengthened.

Since the region in which the electric field is strengthened is considered to be about half of the size of the metal structure particle 203, the size of metal structure particle 203 ranges from 20 nm to 100 nm depending on the size of the target substance. Here, the size of metal structure particle 203 signifies the maximum breadth of metal structure particle 203 in the cross-section parallel to substrate 202 on which metal structures 203 are placed.

Figure 4A:
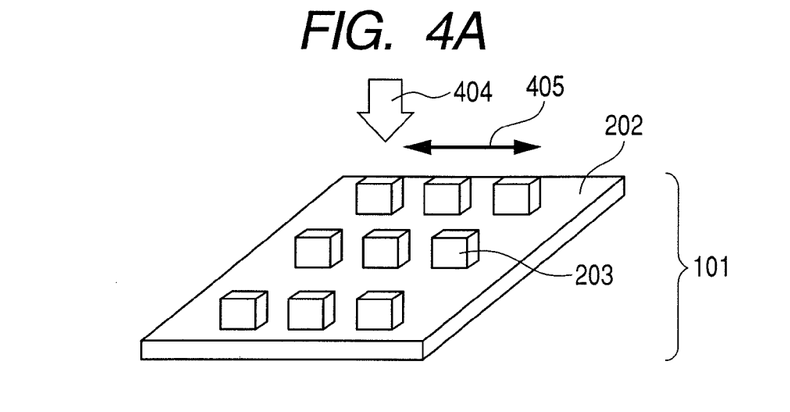
FIG. 4A is a perspective view of an arrangement of the metal structures in the detecting device shown in FIG. 1.
Figure 4B:
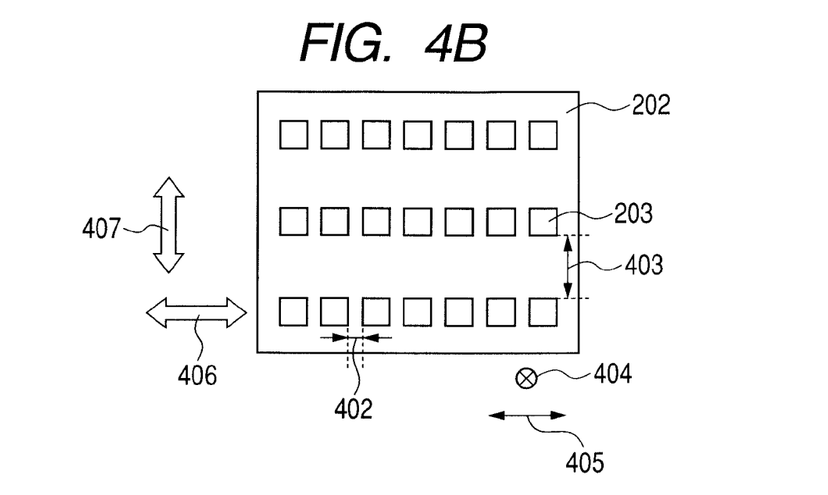
FIG. 4B is a top view of an arrangement of the metal structures in the detecting device of FIG. 1.

Next, the arrangement of metal structures 203 is described with reference to FIGS. 4A and 4B. FIG. 4A is a perspective view of detecting device 101, and FIG. 4B is a top view of detecting device 101 without showing target-substance-capturing body 204. Target-substance-capturing body 204 is provided as necessary, and is not an essential element.

In FIGS. 4A and 4B, metal structures 203 are arranged on substrate 202 at first intervals 402 in lines in first direction 406. Metal structures 203 are arranged also at second intervals 403 in lines in second direction 407 perpendicular to first direction 406. Second interval 403 is made larger than first interval 402.

In the above description, metal structures 203 are arranged on the lines intersecting perpendicularly in first direction 406 and second direction 407. However, first direction 406 and second direction 407 need not be perpendicular to each other, insofar as the directions intersect each other.

Incident light 404 is illuminated onto detecting device 101 preferably in the direction normal to the plane of arrangement of metal structures 203. Further, polarization direction 405 of the incident light is preferably parallel to first direction 406. Thereby, on illumination of incident light 404 onto metal structures 203, the effect of strengthening the electric field is increased in the region of trapping the target substance between metal structures 203 to increase the shift of the plasmon resonance wavelength on capturing the target substance.

Figure 5A:
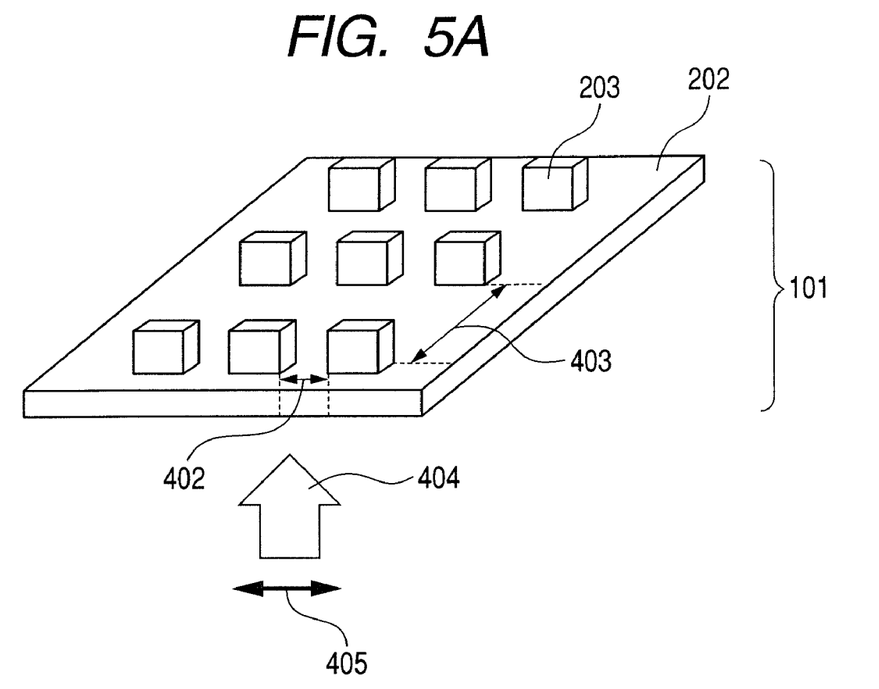
FIG. 5A illustrates schematically an arrangement of the metal structures in electromagnetic field simulation of the detecting device in FIG. 1.
Figure 5B:
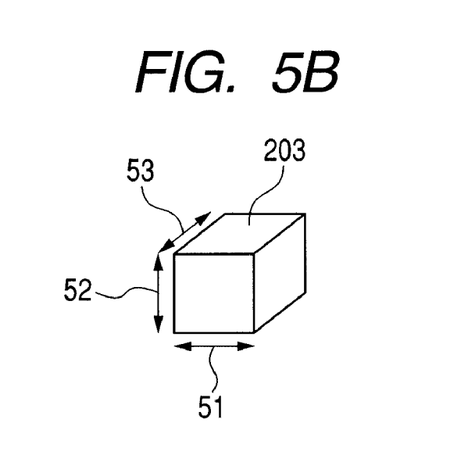
FIG. 5B is a perspective view of a gold structure in the detecting device.

The electromagnetic field simulation is conducted to show the relation between first interval 402 and plasmon resonance wavelength shift, and differential spectrum of the transmittance as the index of performance of detection of the target substance. The simulation is conducted with the constitution of detecting device 101 as illustrated in FIG. 5A. The metal structure particle 203 is illustrated in FIG. 5B: the metal structure particle having width 51, height 52, and depth 53 are respectively of 50 nm, namely being a cube having sides of 50 nm. The conditions for the simulation are shown below, including the constitution of detecting device 101, and the shape of metal structure particle 203.

Metal species of metal structures 203: Gold (Au)
    Shape and size of metal structure particle 203:
        Cube having sides of 50 nm
    First intervals 402: 40 nm, 70 nm, 100 nm, or 130 nm
    Second intervals 403: 450 nm
    Substrate 202: Quartz ($SiO_2$) plate
    Medium surrounding metal structures 203: Water In the simulation, incident light 404 is polarized in polarization direction 405 in first direction 406, and is projected perpendicularly from under substrate 202 to the face of arrangement of metal structures 203.

The surfaces of metal structures 203 are covered with a dielectric film of 10 nm thick as a material of an imaginary target-substance-capturing body. In this state, the transmission spectrum through detecting device 101 is estimated by simulation. Further the surface of the above dielectric film is covered with another dielectric film in a thickness of 10 nm as an imaginary target substance, and the transmission spectrum is estimated by the simulation.

Figure 6A:
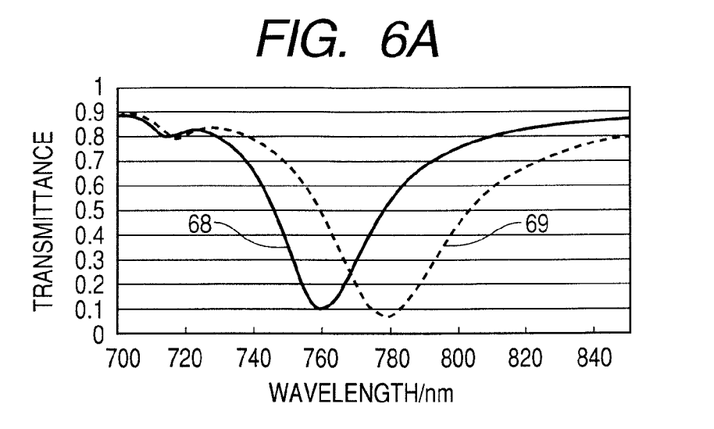
FIG. 6A shows transmission spectra in electromagnetic field simulation.
Figure 6B:
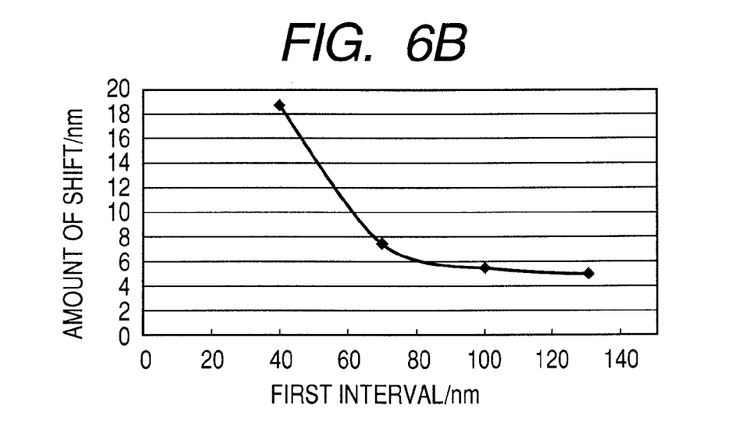
FIG. 6B is a graph showing an amount of shift of the plasmon resonance wavelength.

FIG. 6A shows the estimated transmission spectra before and after the coverage with the dielectric film as an imaginary target substance at first interval 402 of 40 nm. Plots 68 show a spectrum with coverage by the dielectric film of 10 nm thick, and plots 69 show a spectrum with coverage by the dielectric film of 20 nm thick. FIG. 6B shows estimated dependence, on first interval 402, of the shift of the plasmon resonance wavelength by the coverage with a dielectric film as an imaginary target substance. With increase of first interval 402, the amount of the shift of the plasmon resonance wavelength becomes smaller to a certain level asymptotically. This is considered to be due to the fact that the increase of first interval 402 weakens interaction between metal structures 203, retarding the electric field strengthening.

Figure 6C:
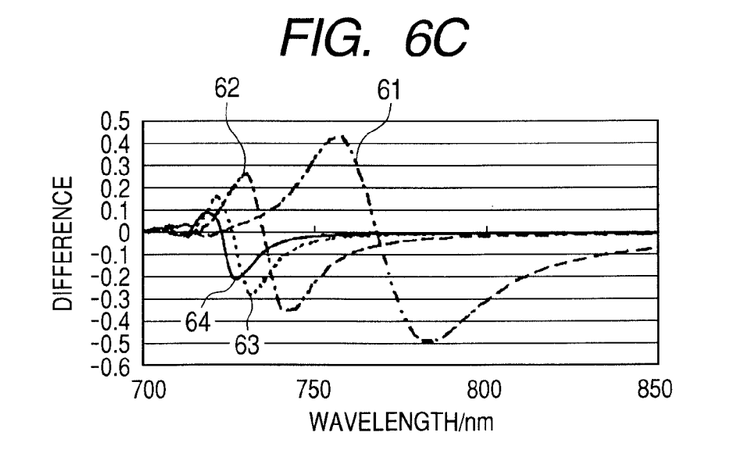
FIG. 6C is a graph showing differential spectra.

FIG. 6C shows the differential spectra, the difference between the transmission spectra before the coverage with the dielectric film as an imaginary target substance and that after the coverage. At the first interval of 40 nm, the peak value of the differential spectra 61 is the largest. In FIG. 6C, the numerals 62, 63, and 64 denote respectively the differential spectrum at the first intervals of 70 nm, 100 nm, or 130 nm. As described above, with increase of the first interval 402, the maximum value of the differential spectrum becomes smaller. In other words, with increase of the amount of the shift of the plasmon resonance wavelength, the maximum value of the differential spectrum becomes larger. With the construction of the detecting device 101 in this simulation, from the relation between of the amount of the shift of the plasmon resonance wavelength and the first interval, the amount of the shift of the plasmon resonance wavelength can be increased in the region where the first interval 402 is smaller than about 80 nm, whereas in the region where the wavelength is larger than 100 nm, the shift amount of the plasmon resonance wavelength is considered to be not increased.

Accordingly, in this simulation, first interval 402 is preferably not larger than about 80 nm. In metal structures 203 in the above simulation, where the surrounding medium is water and a dielectric layer of 10 nm thick covers metal structures 203, the plasmon resonance wavelength is about 760 nm. In consideration of dependence of the plasmon resonance wavelength on the constitution of metal structures 203, first interval 402 is preferably adjusted to be not more than 1/10 of the plasmon resonance wavelength.

However, first interval 402 should have sufficient size for holding both of the target substance and target-substance-capturing-body 204. Therefore, first interval 402 should be not smaller than 1 nm depending on the size of the target substance and target substance-capturing-body 204. If metal structures 203 are brought closer than that, plasmon resonance at the adjacent metal structures 203 can interact each other to lower the localization degree of the aforementioned electric field, causing enlargement of the spectrum peak width. Not to lower the localization degree, first interval 402 is considered to be not smaller than half of the breadth of metal structure particle 203 in first direction 406. Accordingly, first interval 402 is not less than half the breadth of metal structure particle 203 in first direction 406, and not more than 1/10 of the plasmon resonance wavelength.

When first intervals 402 are made smaller as mentioned above, metal structures 203 take nearly a shape of lines arranged in first direction 406. In this state, detecting device 101 is considered to give an effect similar to a slit member having a slit width of second interval 403. With decrease of second interval 403, the detecting device comes to behave as a slit member having a small slit width. The slits intercept an incident light at a wavelength longer than a certain wavelength to lower the transmittance at the long wavelength side. Therefore, when the second interval 403 is small, the intensity of the transmitted light can be made lower to broaden the peak width of the transmitted light.

With metal structures 203 formed in a slit, the relation between the slit width and transmission spectrum is shown by electromagnetic field simulation. In this simulation, the detecting device is assumed to have lines of gold directed to first direction 406, and changes of transmission spectrum is estimated by changing second interval 403. The conditions of constitution of the detecting device, the shape of metal structure particle 203, and so forth are shown below.

Metal species of metal: Gold (Au)
Shape and size of the metal structure:
  Square having a cross-section of 50 nm×50 nm
Second intervals:
  150 nm, 200 nm, 250 nm, 300 nm, or 450 nm
Substrate 202: Quartz (SiO$_2$) plate In the simulation, incident light 404 is polarized in first direction 406, and is illuminated perpendicularly from under the quartz substrate to the face holding the gold slits.

Figure 7:
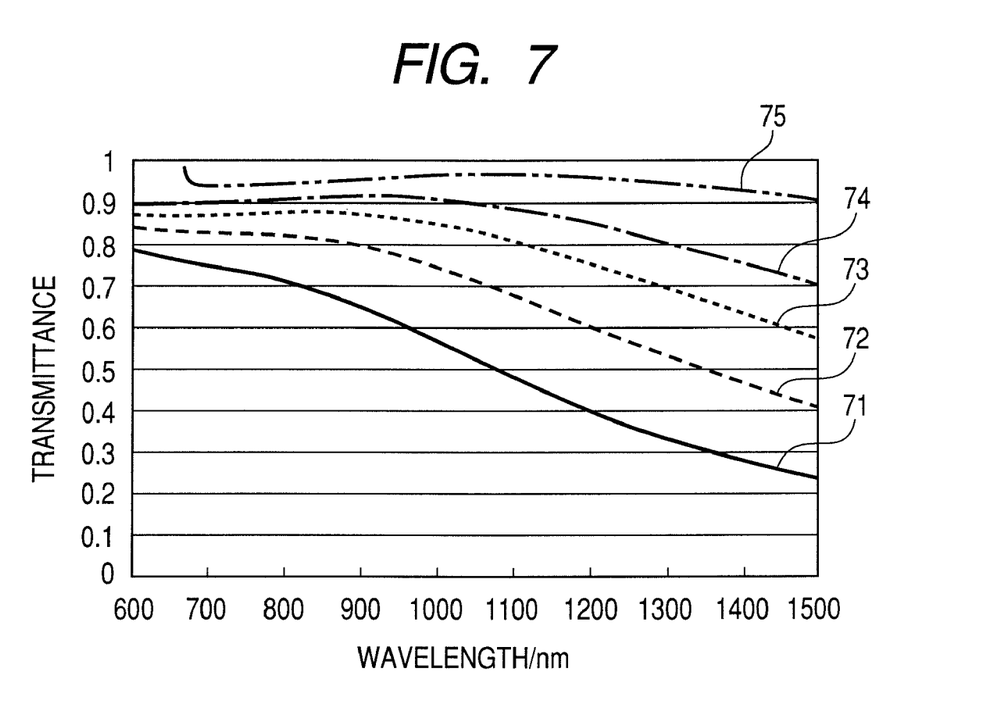
FIG. 7 is a graph of results of electromagnetic field simulation for a gold slit.

FIG. 7 is a graph showing transmission spectra estimated by electromagnetic field simulation for the second intervals. In FIG. 7, spectral curves 71, 72, 73, 74, and 75 denote respectively a transmission spectrum at the second intervals of 150 nm, 200 nm, 250 nm, 300 nm, and 450 nm. FIG. 7 shows that the transmittance is lower at the smaller second interval.

For example, in detecting device 101 having first interval 402 of 40 nm constituted as illustrated in FIGS. 5A and 5B, the plasmon resonance wavelength is about 760 nm as described above. As shown in FIG. 7, the decrease of the transmittance at about 760 nm becomes remarkable at second interval 403 of 150 nm. Therefore, at second interval 403 of 200 nm or less, where the transmittance is lower, the peak width may be increased. Therefore, for raising the sensitivity of detection of the target substance, second interval 403 is preferably not less than 1/4 of the plasmon resonance wavelength.

As described above, an increase of second interval 403 can decrease the slit-effect to result in decrease of the peak width of the spectrum. However, an excessively large second interval 403 can decrease the occupation ratio of metal structures 203 to the area of the illumination to decrease the change of the absorbance by capturing of the target substance. Therefore, second interval 403 is preferably not excessively large.

A transmission spectrum through a device having larger second intervals 403 is estimated by electromagnetic field simulation. The estimation result is described below. In this simulation, detecting device 101 has the constitution similar to that illustrated in FIG. 5A except first intervals 402 and second intervals 403. The conditions for the simulation include the constitution of detecting device 101 and the shape of metal structures 203.

Metal species of metal structures 203: Gold (Au)
Shape and size of metal structure particle 203:
  Cube having sides of 50 nm
First intervals 402: 40 nm
Second intervals 403: 350 nm, 450 nm, 550 nm, 650 nm
Substrate 202: Quartz (SiO$_2$) plate
Medium surrounding metal structures 203: Water In this simulation also, the transmission spectra of metal structures 203 coated with dielectric film of 10 nm thick or 20 nm thick, and the differential spectra thereof are calculated.

Figure 8A:
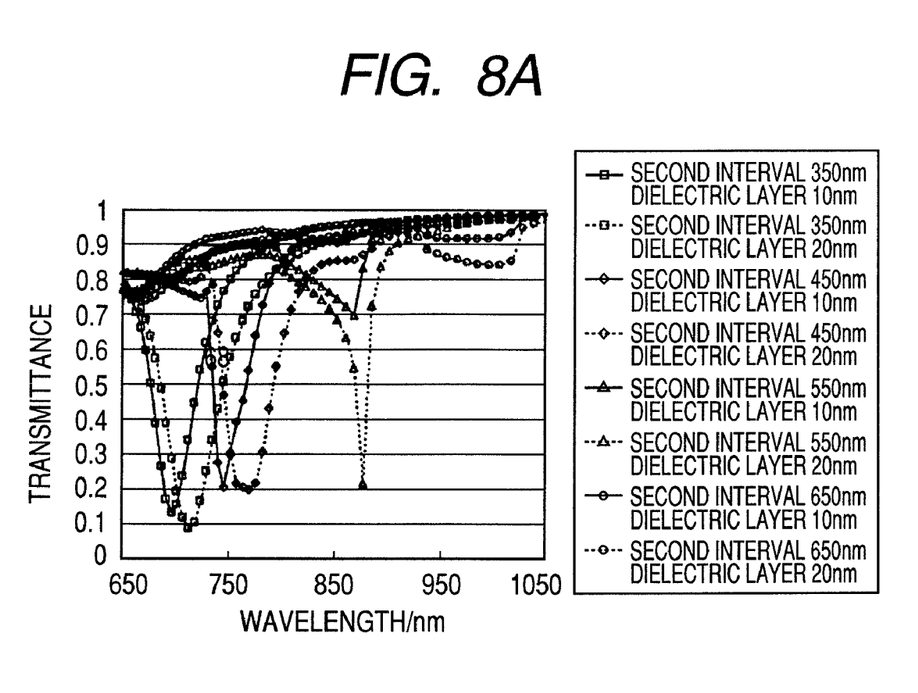
FIGS. 8A and 8B are graphs of results of electromagnetic field simulation.
Figure 8B:
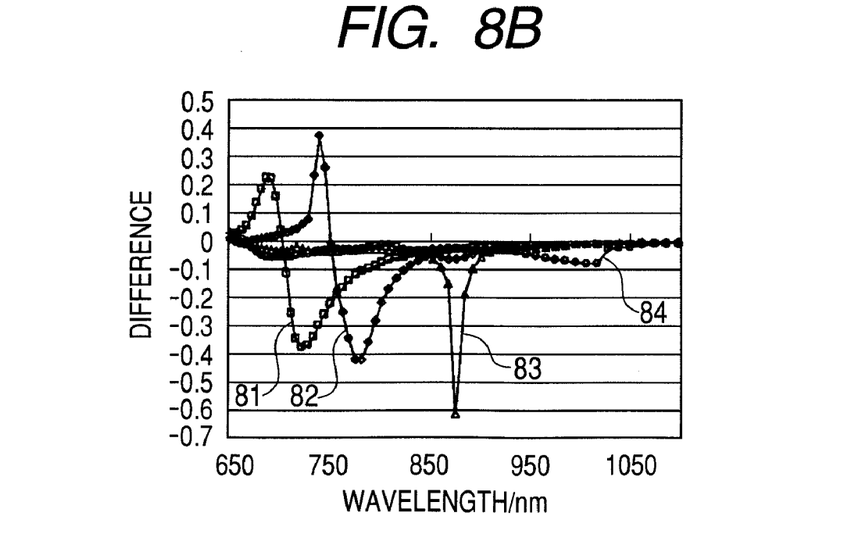

FIGS. 8A and 8B illustrate the simulation results. FIG. 8A is a graph of transmission spectra at respective second intervals 403. The simulation results show that increase of second intervals 403 decreases the occupation region of metal structures 203 to decrease the drop of the transmittance, and that broadening of second interval 403 from 350 nm to 450 nm decreases the spectrum width to increase the difference as the index of the sensor performance.

FIG. 8A shows that decrease of transmittance by the plasmon resonance is small at second intervals 403 of 550 nm with dielectric film of 10 nm thick. However, with the dielectric film of 20 nm thick, drop of the transmittance is larger. FIG. 8B shows the differential spectra 81, 82, 83, and 84 at second intervals of 350 nm, 450 nm, 550 nm, and 650 nm.

Since the absolute value of the difference is large when the second interval 403 is 550 nm, the sensitivity of the detection of the target substance can be improved further.

At second intervals 403 of 650 nm, drop of the transmittance by the plasmon resonance is small, and the absolute value of the difference is small as shown in FIG. 8B to result in a low sensitivity of the detection of a target substance. Therefore the detection apparatus, second interval 403 is preferably less than 650 nm.

From the electromagnetic field simulation, second interval 403 is preferably not less than ¼ of the plasmon resonance wavelength and not more than the plasmon resonance wavelength.

Target-substance-capturing-body 204 immobilized onto metal structures 203 is not limited provided that the capturing body is capable of capturing specifically a target substance. The specific capturing includes any interactions enabling detection of a chemical or physical change caused by contact of the target substance with target-substance-capturing-body 204 immobilized to detecting device 101 of the present invention. Preferred interaction includes antigen-antibody reactions, antigen-aptamer reactions (aptamer: an RNA fraction having a specific structure), ligand-receptor interactions, DNA hybridizations, DNA-protein interactions (e.g., protein including transcription factors), and lectin-sugar chain interactions.

The target substance includes any substance which can be trapped specifically by the target-substance-capturing body by interaction like that as mentioned above and can be detected by detecting device 101.

The target substance and target-substance-capturing body 204 include biological substances. The biological substances include nucleic acids, proteins, sugar chains, lipids, and complexes thereof. More specifically, the target substance and target-substance-capturing body include biological molecules of nucleic acids, proteins, sugar chains, lipids, and complexes thereof, including more specifically DNAs, RNAs, aptamers, genes, chromosomes, cell membranes, viruses, antigens, antibodies, lectins, haptenes, hormones, receptors, enzymes, and peptides. Furthermore, the biological substance includes bacteria and cells which produces the biological substances. That is, the bacteria and cells can be a target substance or target-substance-capturing body 204.

(Illumination Optical System)

Illumination Optical system 102 is not limited, provided that it is capable of illuminating an incident light containing a wavelength range for causing plasmon resonance with metal structures 203 to cross a metal structure-arranged face of detecting device 101. The light source constituting illumination optical system 102 is exemplified by lasers and LEDs. For detecting the shift of the resonance wavelength, a white light source of a broad range is preferred for measurement of the spectrum. The broad-range white light source includes halogen lamps, tungsten lamps, and xenon lamps. For detecting the absorbance change at a specific wavelength, lasers of high output and stable are preferred.

Illumination optical system 102 has preferably a function of polarizing incident light 404 in first direction 406. The electric field between the metal structures 203 in first direction 406 can be intensified effectively by illumination of the incident light polarized in first direction 406 in detecting device 101.

Incident light 404 may be polarized in any method. For example, the incident light 404 from the light source can be polarized by passing through a polarizer.

Incidentally, the target-substance-detecting apparatus of the present invention may have an additional optical system between illumination optical system 102 and detecting device 101. As an example, when the region of arrangement of metal structures 203 is very small in the detecting device, the illuminated light is condensed by providing an optical lens system for adjusting the illumination region or a collimator for optical collimation between the light source and detecting device 101 to enable measurement with small noises.

Any optical system may be placed in any position in the optical path, not being limited to a position between illumination optical system 102 and detecting device 101.

Figure 9A:
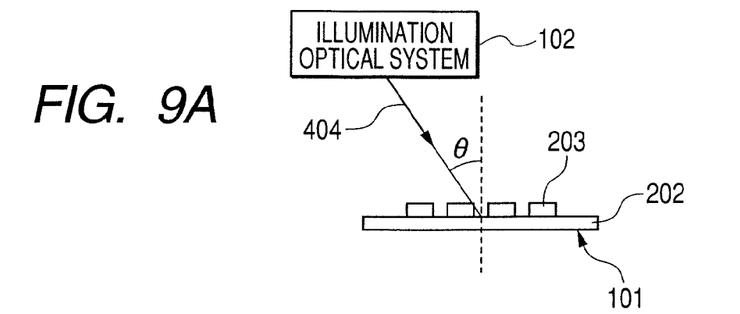
FIGS. 9A, 9B, 9C and 9D illustrate schematically directions of incident light illumination onto a detecting device in a target-substance-detecting apparatus of the present invention.
Figure 9B:
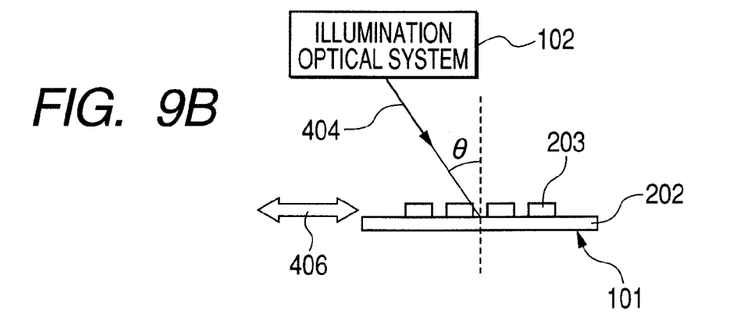
Figure 9C:
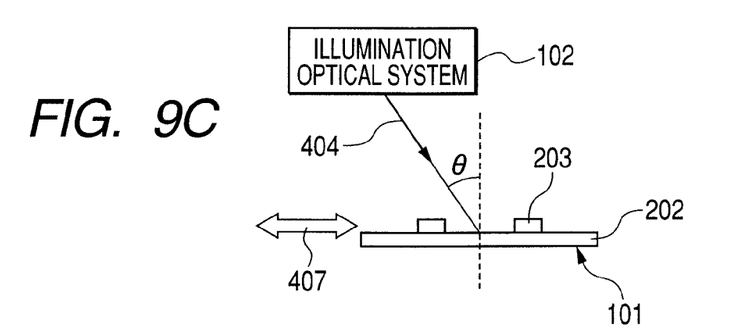
Figure 9D:
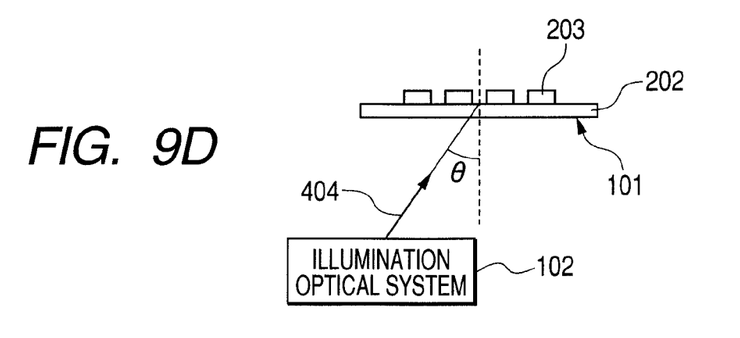

FIGS. 9A, 9B, 9C, and 9D are drawings for describing the direction of illumination of the incident light from illumination optical system 102 to detecting device 101. The direction of illumination of incident light 404 from illumination optical system 102 to the detecting device is not limited, insofar as the light is illuminated onto the face having metal structures 203 of detecting device 101. The incident light may be illuminated perpendicularly to or obliquely to the face of arrangement of metal structures 203. In the oblique illumination, the incident light illumination direction may be oblique to first direction 406 as illustrated in FIG. 9B, or may be oblique to second direction 407 as illustrated in FIG. 9C. Otherwise, the light beam is projected onto substrate 202 from reverse side of arrangement of metal structures 203 as illustrated in FIG. 9D.

(Light-Receiving Device)

Light-receiving device 103 is not limited, insofar as it is capable of detecting optical characteristics such as an intensity and spectrum of the light transmitting through or reflected by detecting device 101. The light-receiving device is selected suitably to detect the change of the characteristic of the detecting light for detection of the target substance. More preferably, the light-receiving device has a function of detecting selectively the polarization component parallel to first direction 406. For this purpose, for example, the light transmitted through or reflected by detecting device 101 is allowed to pass through a polarizer.

A change in intensity of transmitted light can be detected by use of a photodiode, a photo-multiplier tube (PMT), or the like as the light-receiving device. For detection of an extent of a shift of a spectrum of the transmitted light, light-receiving device 103 is preferably mounted on a detector (a spectrometer) employing a spectroscopic optical system. With such a spectroscopic optical system, spectrometry can be conducted by passing the transmitted light from detecting device 101 through a monochrometer, a polychrometer, or a like spectrometer. Otherwise, the wavelength of the incident light illuminated onto detecting device 101 may be varied before illumination of the incident light 404 to detecting device 101 by use of a spectrometric system like a monochrometer to measure the transmission spectrum of the transmitted light. In such a manner the transmission spectrum is measured by detecting the intensity of the transmitted light.

(Arithmetic Unit)

Arithmetic unit 104 is a means for calculating, from a signal derived by light-receiving device 103, a property change of transmitted light or reflected light (hereinafter referred to as detecting light) caused by capturing of a target substance by target-substance-capturing-body 204. The property of the detecting light to be calculated may be an intensity change or spectrum change of the detecting light. Processing of the signals enables estimation of capturing of a target substance from an analyte by target-substance-capturing body 204 on contact of an analyte with metal structures 203 of detecting device 101.

The arithmetic unit has preferably a mechanism for estimating quantitatively the quantity of the target substance by signal processing. For example, preliminarily obtained data of correlation between the quantity of the target substance and the change of the property of the transmitted light are memorized in the arithmetic unit. Thereby, the quantity of the target substance can be calculated by comparing the change of the property of the detecting light caused by the capturing of the target substance from the unknown analyte by target-substance-capturing body 204.

Next, steps in the method for detecting a target substance of the present invention are described below. The method for detecting a target substance of the present invention includes a contact step, an illumination step, a light-receiving step, and a calculation step.

In the contact step, an analyte is brought into contact with the above-mentioned detecting device. A target substance contained in the analyte is specifically captured by the target-substance-capturing body in the detecting device.

In the illumination step, an incident light is illuminated from an illumination optical system to the detecting device. The incident light contains a polarization component polarized in first direction 406. Preferably the illuminated incident light is polarized entirely in first direction 406.

In the light-receiving step, the light transmitted through or reflected by the detecting device is received. Preferably a polarization component polarized in first direction 406 of the transmitted or reflected light is selectively received. On reception of the light, the light-receiving device sends a signal corresponding to the property of the light to the arithmetic device.

In the calculation step, the presence of the target substance in the analyte is calculated from the signal received by the light receiving device. The arithmetic unit has preferably a means for calculating quantitatively the amount of the target substance.

EXAMPLE 1

Figure 10:
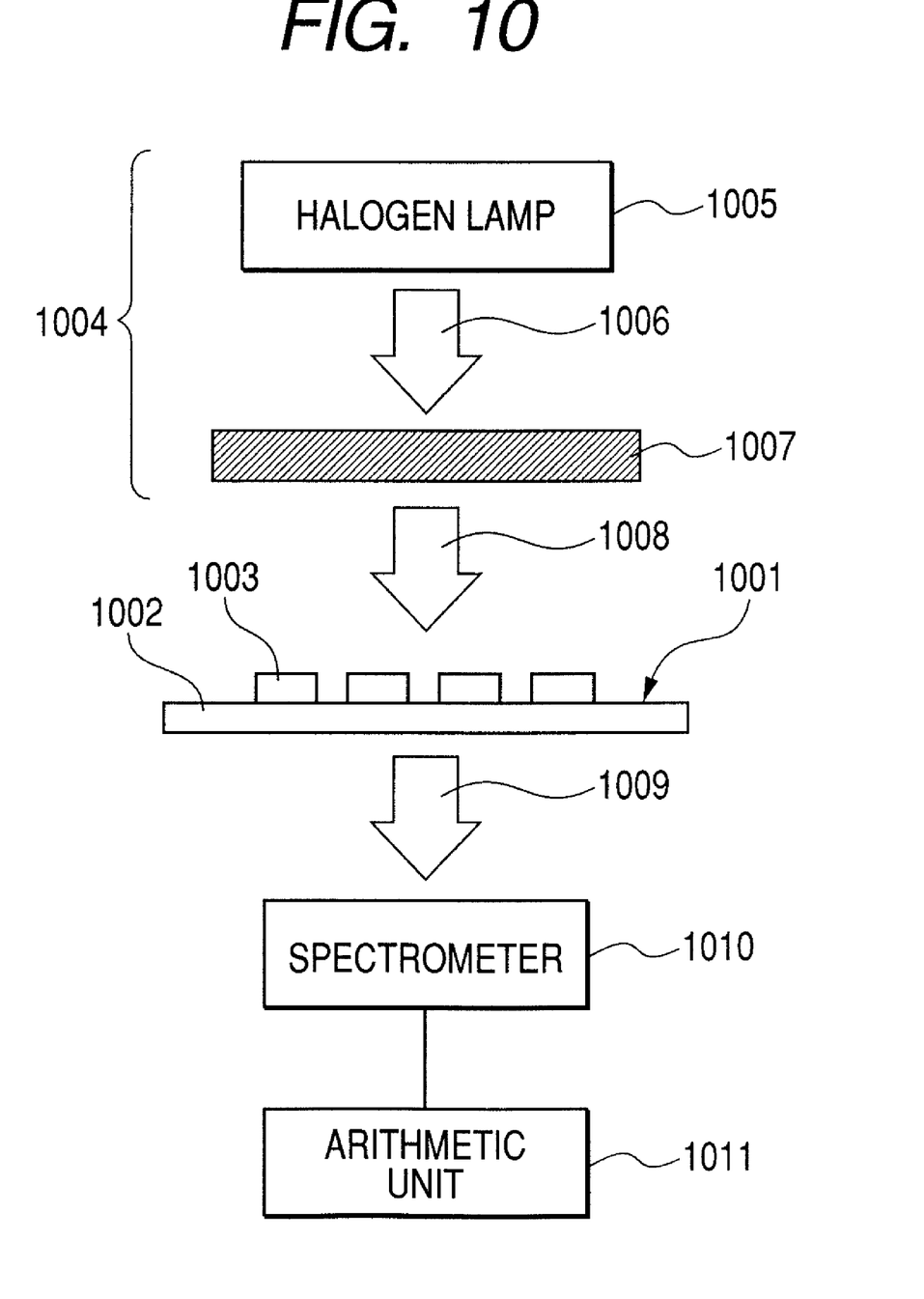
FIG. 10 illustrates schematically a constitution of the target-substance-detecting apparatus of Example 1 of the present invention.

Examples of the target-substance-detecting apparatus and the target-substance-detecting method are described below. FIG. 10 illustrates schematically a constitution of the target-substance-detecting apparatus in this Example. The target-substance-detecting apparatus has a detecting device 1001, illumination optical system 1004 for illuminating an incident light onto detecting device 1001, a light-receiving device for receiving the light transmitted through detecting device 1001, and arithmetic units 1011 for calculation from the signal obtained by the light-receiving device.

In this Example, illumination optical system 1004 is constituted of halogen lamp 1005 and polarizer 1007. Halogen lamp 1005 is useful as a white light source, and polarizer 1007 polarizes white light 1006 emitted from halogen lamp 1005 in a specified polarization direction.

The light-receiving device for receiving transmitted light 1009 from detecting device 1001 has spectrometer 1010. The transmission spectrum of transmitted light 1009 is detected by use of spectroscope 1010. Arithmetic units 1011 has a means for calculating quantitatively the amount of the target substance in the analyte from the signal derived from spectrometer 1010.

Figure 11A:
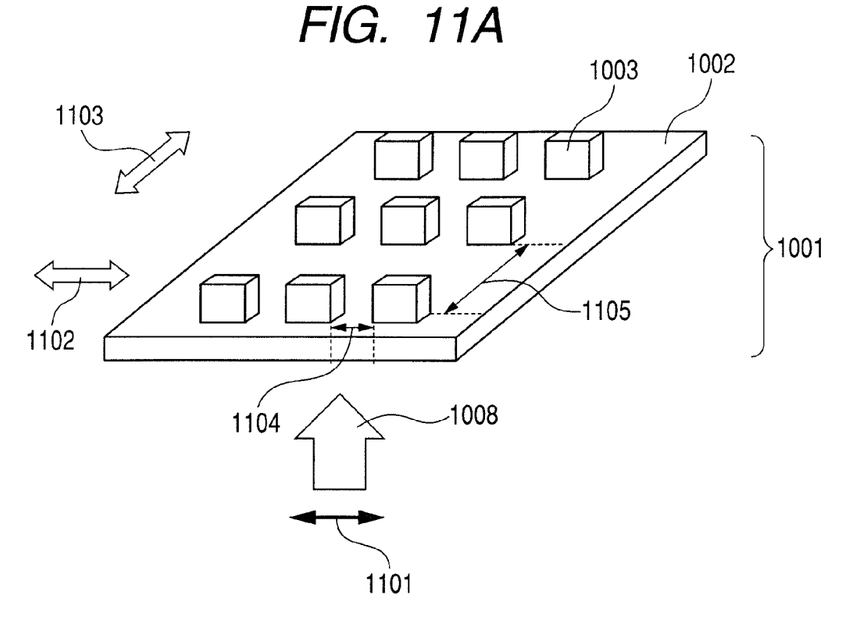
FIG. 11A is a perspective view illustration a constitution of the detecting device of Example 1 of the present invention.

Detecting device 1001 is constituted of quartz substrate 1002 and gold structure 1003 immobilized on the substrate. FIG. 11A is a perspective view of detecting device 1001. Gold structure particles 1003 are arranged on quartz substrate 1002 in first direction 1102 at intervals 1104 of 40 nm in lines, and in second direction 1103 perpendicular to first direction 1102 at intervals 1105 of 450 nm in lines. Gold structure particles 1003 are placed in parallel lines also in second direction 1103.

Figure 11B:
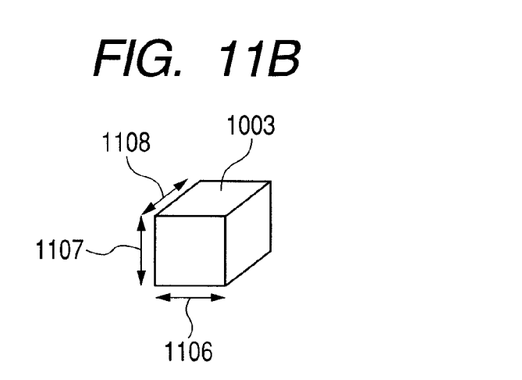
FIG. 11B is a perspective view of the gold structure particle in the detecting device.

The one gold structure particle 1003 is in a shape of a cube having width 1106, height 1107, and depth 1108 of respectively 50 nm: namely a cube of 50 nm sides as illustrated in FIG. 11B. Polarization direction 1101 of illuminated incident light 1008 is adjusted to be directed to first direction 1102.

Gold structure particles 1003 are placed on quartz substrate 1002 in a manner below, as an example. Firstly, thin gold film is deposited in a film thickness of 50 nm on quartz substrate 1002 by sputtering. Then a negative resist is coated on the thin gold film. A resist pattern of squares of 50-nm sides is formed by light exposure by an electron beam lithography apparatus. By utilizing this resist as the mask, the thin gold film on the region not covered by the resist is etched. After the etching, the negative resist used as the mask is removed by an asher. Through this process, gold structure particles 1003 are formed in a shape of cubes of 50 nm sides as illustrated in FIG. 11B.

In the above process, an electron beam lithography apparatus is employed for production of gold structure 1003. However, another apparatus may be employed such as a focused ion beam processor, an X-ray exposure apparatus, an UV-ray exposure apparatus, and excimer exposure apparatus, corresponding to the required working precision and ease of the working. In this Example, gold structure 1003 is formed by etching, but may be formed by a lift-off process.

Figure 12:
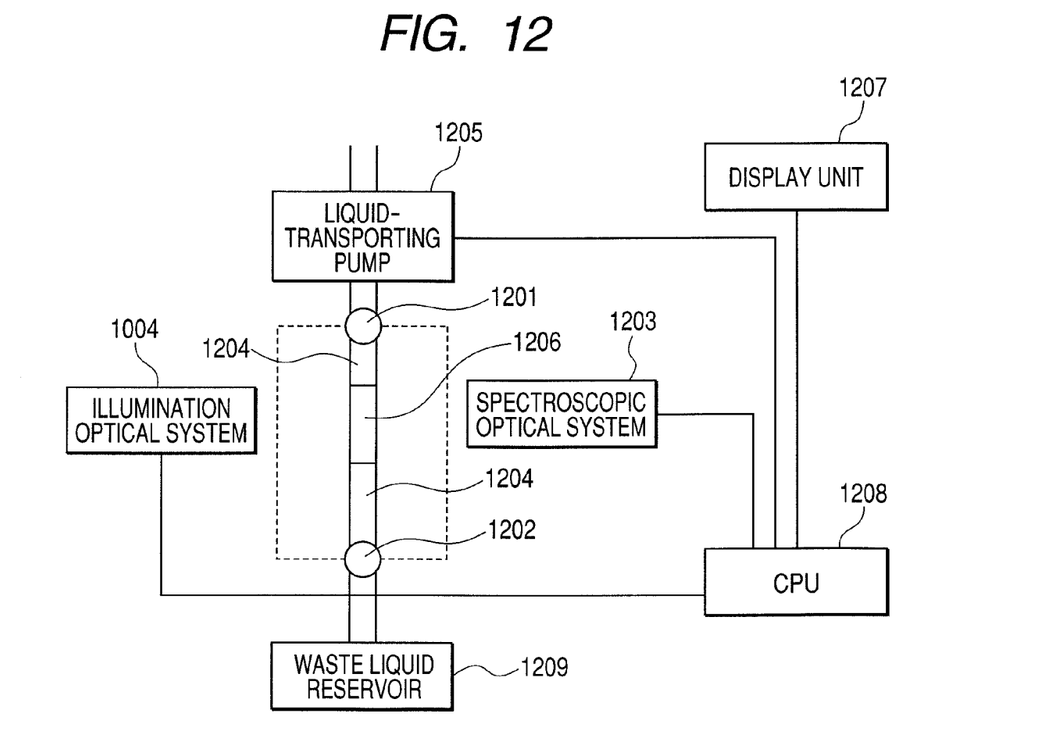
FIG. 12 is a block diagram regarding Example 1 of the present invention.

FIG. 12 is a block diagram illustrating the constitution of the target-substance-detection apparatus of this Example. Arithmetic unit 1011 is constituted of central processing unit (CPU) 1208 and display unit 1207. CPU 1208 is connected to the light-receiving device of spectroscopic optical system 1203 having spectrometer 1010 to receive signals therefrom. Region 1206 which contains gold structure 1003 on substrate 1002 of detecting device 1001 is placed on the optical axis of illumination optical system 1004 and the light-receiving device. Polarization direction 1101 of the incident light 1008 illuminated from illumination optical system 1004 and first direction 1102 light direction are designed to coincide with each other. Detecting device 1001 is tubular, and contains gold structure 1003 placed on a plane inside the tube. The both ends of the detecting device 1001 are connected respectively to tubular members 1204 having a similar shape. One of cylindrical members 1204 has inlet opening 1201 for introduction of the analyte. The other one of cylindrical members 1204 has outlet opening 1202 for discharging the analyte, and outlet opening 1202 is connected to waste liquid reservoir 1209. Liquid-transporting pump 1205 is connected to one of the cylindrical members 1204. This pump serves to transport the introduced analyte through region 1206 containing gold structure 1003 to outlet opening 1202. Inlet opening 1201 and outlet opening 1202 are used for injection of an analyte as well as immobilizing the target-substance-capturing body on gold structure 1003.

An example is described in which a human CRP is detected as the target substance by use of an anti-human-CRP antibody as the target-substance-capturing body. Firstly, a process for immobilizing the anti-human-CRP antibody onto gold structure 1003 of the target-substance-detecting apparatus is described. An ethanol solution of 11-Mercaptoundecanoic acid having a thiol group highly affinitive to the gold is introduced into inlet opening 1201 by driving the liquid-transporting pump to modify the surface of gold structure 1003 placed inside the detecting device 1001. Thereafter two kinds of aqueous solutions are introduced through inlet opening 1201. The introduced two aqueous solutions are an aqueous solution of N-Hydroxysulfosuccinimide, and an aqueous solution of 1-Ethyl-3-[3-dimethylaminopropyl]carbodiimide hydrochloride: the both aqueous solutions are made by Dojin Kagaku Kenkyusho. The contact of the above aqueous solutions with gold structure 1003 in detecting device 1001 bares the succimide group on the surface of gold structure 1003. Then through inlet opening 1201, is introduced a tris-hydrochloric acid buffer solution (pH 8.0) containing an anti-human-CRP antibody capable of capturing specifically the human CRP, the target substance. Thereby the anti-human-CRP antibody is immobilized onto gold structure 1003.

The method for detecting the human CRP in the analyte is described below. Before capturing the human CRP by the anti-human-CRP antibody, the steps of light illumination and light reception are conducted preliminarily. In the step of the light illumination, incident light 1008 is illuminated onto the face having gold structure 1003 of detecting device 1001. In the step of the light reception, light 1009 transmitted through detecting device 1001 is received, and the spectrum of transmitted light 1009 is detected by spectroscopic optical system 1203.

Next, a contact step is conducted. In this step an analyte containing a human CRP is introduced through inlet opening 1201 into region 1206 of detecting device 1001 containing gold structure 1003. Thereby the human CRP in the analyte is selectively captured by the anti-human-CRP antibody immobilized to gold structure 1003.

After that, the steps of light illumination and light reception are conducted again, and the spectrum of transmitted light 1009 after the capturing of the human CRP is detected by spectroscopic optical system 1203.

Finally, as the calculation step, spectra of transmitted light 1009 before and after trapping of the human CRP are compared by central processing unit 1208 of arithmetic unit 1011. The obtained change of the spectrum of transmitted light 1109 results from change of the plasmon resonance spectrum caused by capturing of the human CRP by the anti-human-CRP antibody. The calculation result of the spectrum change is displayed on display unit 1207.

In this Example, central processing unit 1208 calculates the concentration of the target substance from the extent of change of the spectrum of transmitted light 1009. The concentration of the target substance can be calculated, for example, as below. Preliminarily, with analytes of known concentrations, the relation of the change of the spectrum of transmitted light 1009 with the concentration is derived. Therefrom a calibration curve, and a correlation function of the change of the spectrum of transmitted light 1009 and the concentration are derived. Based on the function, the unknown concentration of the target substance can be calculated from the spectrum change obtained in the calculation step.

The spectrum change may be a change of the wavelength of the maximum (spectrum peak) of the absorbance, or a change of the peak shape such as a half width of the spectrum peak, or change of absorbances at one or more wavelengths.

In this Example, the target substance is detected through the aforementioned order of the steps. However, the order of the steps is not limited, provided that the change of the transmitted light spectrum caused by capturing of the target substance can be calculated. The steps need not be conducted separately. In this Example, the concentration is calculated from the change of transmission spectrum of the light transmitted through the detection device. Otherwise the concentration may be calculated from the change of spectrum of the light reflected by the detecting device.

The present invention is not limited to the above embodiments and examples. The materials, composition conditions, the reaction conditions, the arrangement of the members and elements in the above embodiments and examples may be modified within the range of understanding of a person skilled in the art to practice the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-254744, filed Sep. 28, 2007, which is hereby incorporated by reference herein in its entirety.

The invention claimed is:

1. A target substance-detecting apparatus for detecting a target substance in an analyte, comprising:
   a detecting device having a substrate on which metal structures capable of causing a plasmon resonance are arranged,
   an illumination optical system having a mechanism for illuminating an incident light containing a polarization component polarized in a first direction onto the detecting device to cross the arranged metal structures in the detecting device,
   a light-receiving device for receiving light containing the polarization component polarized in the first direction and transmitted through or reflected by the detecting device, and
   an arithmetic unit for calculating on signals from the light-receiving device to analyze a characteristic of the analyte;
   the metal structures being arranged at first intervals in lines in the first direction and at second intervals in lines parallel in a second direction intersecting the first direction, the first intervals being not more than $1/10$ of a plasmon resonance wavelength, and the second interval being not less than $1/4$ of the plasmon resonance wavelength and not more than the plasmon resonance wavelength.

2. The target substance-detecting apparatus according to claim 1, wherein the metal structures are arranged in the first direction and in the second direction, the first direction and the second direction being perpendicular to each other.

3. The target substance-detecting apparatus according to claim 1, wherein the structure particle of the metal structures has a size of not smaller than 20 nm and not larger than 100 nm.

4. A method for detection of a target substance for detecting a target substance in an analyte, comprising the steps of:
   bringing the analyte into contact with a detecting device having a substrate on which a metal structures capable of causing a plasmon resonance are arranged,
   illuminating an incident light containing a polarization component polarized in a first direction onto the detecting device to cross the arranged metal structures in the detecting device,
   receiving light containing the polarization component polarized in the first direction and transmitted through or reflected by the detecting device, and
   calculating on signals from the light-receiving device to analyze a characteristic of the analyte;
   the metal structures being arranged at first intervals in lines in the first direction and at second intervals in lines parallel in a second direction intersecting the first direction, the first intervals being not more than $1/10$ of a plasmon resonance wavelength, and the second interval being not less than $1/4$ of the plasmon resonance wavelength and not more than the plasmon resonance wavelength.

* * * * *